United States Patent [19]

Callahan et al.

[11] 4,303,550

[45] Dec. 1, 1981

[54] METHODS FOR THE REGENERATION OF DEACTIVATED PHOSPHOMOLYBDIC ACID BASED CATALYSTS

[75] Inventors: James L. Callahan, Wooster; Wilfrid G. Shaw; Arthur F. Miller, both of Lyndhurst, all of Ohio

[73] Assignee: Standard Oil Company, Ohio

[21] Appl. No.: 107,989

[22] Filed: Dec. 28, 1979

[51] Int. Cl.³ .................. B01J 27/28; C07C 51/25; C07C 57/055

[52] U.S. Cl. .................. 252/413; 252/412; 252/415; 562/532; 562/534; 562/535

[58] Field of Search ............ 252/412, 413, 414, 415, 252/435, 437; 562/532, 534, 535

[56] References Cited

U.S. PATENT DOCUMENTS

| | | | |
|---|---|---|---|
| 1,923,652 | 8/1933 | Winkler et al. | 252/414 |
| 2,973,326 | 2/1961 | Hodgins et al. | 252/412 |
| 4,083,805 | 4/1978 | White | 562/535 |
| 4,138,366 | 2/1979 | Shaw et al. | 252/435 |
| 4,165,296 | 8/1979 | Ishii et al. | 252/412 |

Primary Examiner—P. E. Konopka
Attorney, Agent, or Firm—Joseph G. Curatolo; Larry W. Evans; Herbert D. Knudsen

[57] ABSTRACT

The present invention relates to a method for the regeneration of deactivated PMA based catalysts by imbibing an aqueous volatile base within the pore structure of the deactivated catalyst so as to form a fluid phase within the pore structure, adding a volatile acid to the fluid phase to form a precipitate. The precipitate is thereafter dried and calcined to yield the regenerated catalyst. A second method for regeneration is also provided and includes the steps of imbibing a volatile solvent within the pore structure of the deactivated catalyst, adding a volatile acid to the system, and then adding a volatile base to the system to form a precipitate within the pore structure. The precipitate is again dried and calcined to yield the regenerated catalyst.

25 Claims, No Drawings

METHODS FOR THE REGENERATION OF DEACTIVATED PHOSPHOMOLYBDIC ACID BASED CATALYSTS

TECHNICAL FIELD

Catalysts comprising phosphomolybdic acid and various salts thereof have recognized utility in several areas of petrochemical processing. An area of particular importance and which relates to the present invention is the use of phosphomolybdic acid based compounds as catalysts for the selective direct oxidation of unsaturated aldehydes such as methacrolein to its corresponding acid methacrylic acid. Catalysis with supported or unsupported dehydrated phosphomolybdic acid in combination with small amounts of promoters such as antimony, arsenic, bismuth, copper, tellurium and hydroxides or decomposable salts of alkalis and alkali earth metals, is a process of specific economic interest.

It has become well known that phosphomolybdic acid (PMA) and salts thereof are sensitive to significant structural change caused by thermal, hydrolytic or reductive stress. As is to be expected, such physical and chemical changes caused by these stresses are directly reflected in a reduction in catalytic activity. Thus, it has not been uncommon for much of the catalytic activity to be lost after only a relatively short on-stream time.

It is believed that deactivation of PMA based catalysts can occur by processes which cause loss of acid sites via condensation crosslinking. A fully deactivated catalyst will be analogous to the anhydride of $P_2O_5$, which contains no free -OH groups. Contacting an active deammoniated PMA based catalyst with moisture below about 100° C. is a certain means of causing deactivation. In this temperature range water vapor undergoes capillary and surface condensation within the catalyst particles. This fluid phase provides for mass transport within the structure so that deactivating condensation can and does occur. Generally, shut-down of the reactor can be marked by a significant decrease in catalytic activity.

In addition to the cooling down deactivation, other processes that can cause mass transport and result in deactivating condensation crosslinking are deep reduction and thermal excursion. Overheating of the catalyst can also result in complete decomposition of the acid structure to its component oxides $MoO_3$ and $P_2O_5$. While the occurrence of these deactivations can be minimized by avoiding reactor shut-down and otherwise controlling the catalytic process, nevertheless, deactivation inevitably occurs. In fact, in the conversion of methacrolein to methacrylic acid, significant loss of catalytic activity can be noted after only a few weeks of use.

The subject invention relates to methods for the effective regeneration of PMA based catalysts having been deactivated in the foregoing conversion of aldehyde to acid either by crosslinking or thermal excursion leading to partial or total loss of the PMA structure. In order for the catalyst regeneration to be practical from a consideration of technical as well as economic aspects, it is desirable that the regeneration scheme be practiced without necessitating reactor shut-down and catalyst removal or, in the case of a fluid-bed operation, that regeneration be capable of execution in a conventional regenerator vessel. This restriction therefore dictates that the deactivated catalyst be regenerated in the vapor phase.

BACKGROUND ART

While much have been published or patented on the subject of PMA based catalysts and their uses as oxidation catalysts and, regeneration of other catalysts is generally known, very little prior work directed toward the regeneration of PMA based catalysts has been reported. Two references of which we are aware involve Japanese authors. One of these, a Japanese patent application, No. 77/29,660, filed by Mitsubishi Rayon Co., Ltd., describes the regeneration of a PMA based catalyst by treatment with ammonium hydroxide, and hydrogen peroxide or ozone and optionally also with nitric acid or ammonium nitrate. The inventors reported that the initial oxidation of methacrolein with the fresh catalyst gave 88% methacrylic acid with 66% conversion of methacrolein; the spent catalyst gave only 71.5% methacrylic acid with 30.3% conversion of methacrolein and, that following regeneration with ammonium nitrate and ammonium hydroxide and 5 parts of 30% hydrogen peroxide for 30 minutes at 90° C., the catalyst gave 88.1% methacrylic acid with 65.1% conversion of methacrolein. This process is undesirable inasmuch as it merely attempts to oxidize the deactivated catalyst and to do so outside of the reactor, necessitating shut-down.

The second of the references is another Japanese patent application, No. 77/66,629, filed by Japan Synthetic Rubber Co., Ltd., and describes the regeneration of spent catalysts containing oxides of molybdenum, phosphorous and vanadium and one or more of potassium, rubidium, cesium and thallium utilized in the oxidation of methacrolein to methacrylic acid. Regeneration was accomplished by treating with hydrochloric acid at 0° to 200° C. for more than 30 minutes followed by calcining in air or oxygen. The fresh catalyst initially gave 55.3% yield of methacrylic acid with 85% conversion of methacrolein; for the spent catalyst, yield and conversion dropped to 37.4% and 53.1%, respectively; however, following regeneration of the catalyst, yield and conversion were increased to 54% and 81.2%, respectively. Unfortunately, this process includes operation in the liquid phase and is therefore not as desirable as regeneration in the vapor phase which can take place within the reactor.

To be useful, we believe the regeneration of PMA based catalysts must occur in the vapor phase, and whether inside or outside of the reactor, without catalyst removal. It is also necessary to reactivate the catalyst in a manner that is compatible with a fluid-bed process. In such an instance, even though the life of the catalyst were on the order of one month, only a small slip stream sufficient to turn the charge over several times per month would be sufficient for regeneration. The regenerator could actually be quite small and fabricated from conventional corrosion resistant materials.

DISCLOSURE OF THE INVENTION

It is therefore an object of the present invention to provide a method for the regeneration of PMA based catalysts utilized in the oxidation of unsaturated aldehydes to acids.

It is another object of the present invention to provide a method for readily regenerating PMA based catalysts utilizing a slip stream so as not to interrupt production.

It is yet another object of the present invention to provide a method for regenerating PMA based catalysts in the vapor phase.

It is still another object of the present invention to provide a method for regenerating PMA based catalysts that have undergone thermal excursion and total breakdown or extensive crosslinking of acid sites.

It is a further object of the present invention to provide a separate method for regenerating PMA based catalysts that have undergone only mild crosslinking of acid sites and which method incorporates several of the foregoing objects.

These and other objects, together with the advantages thereof over known methods, which shall become apparent from the specification which follows, are accomplished by the invention as hereinafter described and claimed.

In general one method of the present invention involves the steps of imbibing an aqueous volatile base within the pore structure of the deactivated catalyst so as to form a fluid phase within the pore structure of the catalyst, adding a volatile acid to the fluid phase to form a precipitate and thereafter drying and calcining the treated catalyst. Although the regeneration is preferably conducted in vapor phase to avoid problems such as caking of the catalyst within the reactor or regenerator, a fluid phase is necessary during the base-acid treatment to permit separation of crosslinked chains and prevent recrosslinking during final activation. By operating within a given pressure range, it is possible to create a fluid phase regeneration within the catalyst particle pores while more broadly conducting a vapor phase regeneration.

While the foregoing method is operable on catalysts that have been deactivated solely by crosslinking or by thermal excursion or both, an alternative method is also disclosed whereby PMA based catalysts deactivated only by crosslinking can be regenerated. This method involves the steps of imbibing a volatile solvent within the pore structure of the deactivated catalyst adding a volatile acid to the system, then adding a volatile base to form a precipitate within the pore structure, and thereafter drying and calcining the treated catalyst. The method is also more suitable than the first for the regeneration of high alkali content PMA catalysts.

PREFERRED MODE FOR CARRYING OUT THE INVENTION

The catalyst commonly employed in the preparation of methacrylic acid from methacrolein and possibly acrylic acid from acrolein is a PMA based catalyst which can be provided with one or more metallic promoters and which has the general formula $Mo_xP_yA_aB_bC_cD_dE_eO_z$. Suitable promoters include the following: where A is ammonium, cesium, potassium, rubidium and/or thallium; B is copper and/or vanadium; C is antimony, arsenic, bismuth and/or tellurium; D is palladium; E is aluminum, barium, calcium, cerium, chromium, cobalt, iron, magnesium, manganese, nickel, tantalum, titanium, tungsten, zinc, zirconium, chlorine and/or bromine; and, wherein x can be 6 to 14 and is preferably 12, y can be 0.1 to 15 and is preferably 1 to 1.5, a can be 0.1 to 3 and is preferably 1 to 2, b can be 0.1 to 3 and is preferably 0.1 to 1, c can be 0 to 2 and is preferably 0 to 0.7, d can be 0 to 2 and is preferably 0 to 1, e can be 0 to 4 and is preferably 0 to 1, and z is a number necessary to satisfy the other elements. Suitable catalysts and the preparation thereof have been described in several U.S. patents commonly owned by the Assignee of record herein and include, for instance, U.S. Pat. Nos. 4,083,805 and 4,138,366. Of these many catalysts, those having a ratio of molybdenum to phosphorous of from about 3:1 to as high as 15:1 can be employed with 9 to 12:1 being preferred.

The conversion of aldehyde to acid is accomplished with molecular oxygen, conducted directly to the reaction vessel, or supplied as air. The oxygen and aldehyde reactants are preferably carried by steam with the foregoing reactants collectively being referred to as the reactant feed. The steam can optionally be replaced by recycle gases from the reactor which would normally include nitrogen, oxygen, carbon oxides and other gases which would also comprise a portion of the reactant feed. In some oxidation systems, the reactant feed could also include the effluent from a first stage reactor wherein isobutylene is principally converted to methacrolein. When the effluent comprises the reactant feed, it will be understood that other components will also be present; several that are by-products of the first stage conversion and others such as air which would normally be added for the conversion of methacrolein.

The conversion reaction can be conducted in either a fixed-bed or fluid-bed reactor at temperatures of from about 200° C. to about 400° C. and pressures of about 0.2 to about 10 atmospheres. The catalyst may be in a supported or unsupported form; suitable support materials including silica, alumina, boron-phosphate, titania, zirconia and the like and preferably Alundum as well as mixtures thereof. The catalyst can have any of the conventional fixed-bed forms such as coated, tablet, pellet, extruded, spherical, or fluid-bed forms such as microspherical or other forms known in the art. Presence of the catalyst increases the rate and percent of conversion; the selectivity of the reaction, wherein the aldehyde to acid conversion is favored; and the single pass yield.

In normal use, the apparent contact time of feed over catalyst in the reactor can vary from about a fraction of a second to as many as 20 or more. A charge of fresh catalyst will remain active for approximately one to two months after which time a marked decrease in conversion single pass yield and selectivity is observed. In order to improve these, the catalyst can be regenerated according to either of the methods of the present invention.

Regeneration includes the steps of treating the deactivated catalyst with an aqueous vapor of a volatile and decomposable base and acid. Bases having utility in the present invention include ammonia, amines such as trimethylamine, tetraalkyl ammonium hydroxides having from four to about 16 carbon atoms and other free bases having a pH of at least 8 and which are capable of decomposing any residual PMA structure in the deactivated catalyst to form a molybdate salt of the base.

Following treatment with an aqueous base, the next step is treatment with an aqueous, volatile and decomposable acid. Purpose of the acid is to neutralize a large proportion of the base and thereby establish conditions for the formation of PMA and/or its salt of the decomposable base. Such acids suitable for the second step include hydrochloric acid and organic carboxylic acids having from 1 to about 4 carbon atoms including halogenated acids such as trichloroacetic acid. In addition to hydrochloric acid, other mineral acids such as hydrobromic, hydroiodic and nitric can be employed.

The preferred base and acid respectively are ammonia and hydrochloric acid, both of which are in admixture with water vapor or other suitable polar solvent vapor such as lower alcohols; aqueous solutions of the base and acid being particularly preferable.

A temperature at which uncondensed solvated PMA or its salt is thermodynamically favored must be employed, which temperature is used for the treatment with the volatile base and volatile acid and is, in turn, crucial to the efficiency of the regeneration. Generally, temperatures above about 50° C. and lower than about 200° C. constitute the range for effective regeneration.

The relative pressure of the aqueous base and acid vapors is preferably within the range of 0.2 to 0.95. Relative pressure is the decimal fraction of the pressure required for gross condensation of the aqueous vapor. At 100° C. and one atmosphere of pressure, gross condensation of water will occur and the value of one can be assigned. A relative pressure of less than 0.2 does not provide sufficient capillary and surface condensation of vapor within the catalyst particles to be optimally effective, whereas at relative pressure greater than 0.95, gross condensation between catalyst particles and the regeneration vessel may take place. Gross condensation of this nature may lead to removal of the catalyst from its support, caking of the catalyst and possibly, corrosion of the regeneration vessel.

The optimum relative pressure will produce a significant fluid phase within the catalyst particles with little or no fluid phase external to the particles themselves. Although a liquid phase external to the particles may be impractical, it is nevertheless necessary within the catalyst particles for satisfactory regeneration. Inasmuch as a deactivated catalyst is crosslinked to a high degree, the PMA units exist as tightly packed chains rather than being largely separated as in the active catalyst. For regeneration, a means must be provided to separate the chains after the crosslinks have been hydrolyzed and reacted with ammonium ions. The fluid phase provides such a means, serving as a vehicle for the mass transport of the hydrolyzed chains wherein much of the energy required for chain movement is derived from the heat of hydration and like-charge repulsion in the ionic fluid. Thus, while vapor phase regeneration will hydrolyze the crosslinks satisfactorily, if the chains do not separate, they will recrosslink upon de-ammoniation with acid resulting in little or no regeneration.

In order to avoid problems attendant total liquid phase regeneration, vapor phase regeneration can be employed so long as the relative pressure is within the foregoing range. The ensuing restricted condensation within the catalyst is sufficient to provide enough of a fluid phase for crosslinked chain separation upon hydrolysis.

In the examples which follow, a liquid phase regeneration of deactivated PMA catalyst powder is reported, followed by vapor phase regenerations of the same catalyst once as a powder and again on an Alundum carrier. In order to evaluate the effectiveness of the method set forth herein, a measurement of percent per single pass yield or percent yield (% Yield) was made, which is defined as follows:

$$\text{Percent Single Pass Yield} = \frac{\text{Moles of product recovered}}{\text{Moles of methacrolein fed}} \times 100$$

Testing was conducted with a sample catalyst that had suffered substantial deactivation. The catalyst, $Mo_{12}PAs_{0.5}Cu_{0.25}O_z$, coated on Alundum, had been used in a pilot plant run for 140 hours. It was washed off of the support with water, then coated on 10-20 mesh Alundum particles and tested, providing only an 11.0% Yield which is essentially inactive. Conversion of methacrolein to methacrylic acid was in a microreactor at 375° C. with a contact time of one second.

Testing was conducted in a flow microreactor consisting of a 0.79 cm I.D.×16.51 cm long stainless steel tube immersed in a molten salt bath at 375° C. and atmospheric pressure. Reactant feed comprising air, water and isobutylene, molar ratio of 12:3:1, was introduced into the bottom of the reactor through a 0.48 cm O.D. stainless steel preheat leg; the reactor and preheat leg forming a U-tube configuration. Within the reactor was a suitable first stage catalyst for the conversion of isobutylene to methacrolein on top of which was stacked the candidate second stage catalyst for the conversion of methacrolein to methacrylic acid. Process water was fed through a silicone rubber septum at the top of the preheat leg with a model 355 Sage syringe pump being used to regulate the process water flow rate. First stage conversion, i.e., isobutylene to methacrolein, was conducted by feeding isobutylene, air and water through the microreactor for an apparent contact time with 4 cc of the first stage catalyst of two seconds. Composition of the particular first stage catalyst employed was 20% silica and 80% active ingredients, the latter comprising $Cs_{0.5}Ni_{2.5}Co_{4.5}Fe_3Bi_1Sb_{0.5}Mo_{12}O_z$. Results of the first stage oxidation were 98% total conversion with 76% Yield of methacrolein, 11% methacrylic acid and the remainder being oxides of carbon. For the second stage conversion, methacrolein to methacrylic acid, an apparent contact time of one second was provided. The second stage catalyst was at the 28.6 weight percent level, supported on 10-20 mesh Alundum particles.

Example No. 1

0.5 gm of an unsupported completely deactivated catalyst powder (less than 15% Yield of MAA in the above test) was slurried in water and a stoichiometric amount of $NH_4OH$ was added to combine with each molecule of molybdenum to form $(NH_4)_2MoO_4$. After about 15 minutes of stirring and heating it was observed that the color of the originally near black slurry had changed to a nearly clear robin's egg blue indicating that the molybdenum had been dissolved and completely reoxidized. The light blue tint of the solution was attributed to the small amount of copper present. Next the pH of the solution was adjusted to about 3 by the drop-wise addition of HCl. This adjustment caused the precipitation of insoluble ammonium phosphomolybdate and caused the color to change to a light yellow with a green tint. The solution mixture was evaporated and the resulting powder was coated on 10-20 mesh Alundum particles using substantially anhydrous ethanol as a wetting fluid. After calcining at 320° C., the catalyst was tested with the first stage catalyst resulting in a 44.0% Yield of methacrylic acid based upon isobutylene in the reactant feed. Conversion of this order is in the range of a fresh active catalyst of the same composition and so it can be stated that activity restoration was essentially complete. While this work established the operability of the method, a vapor phase regeneration will have greater practicality for regenerations of the type comtemplated herein and accordingly, examples of such follow.

Example No. 2

0.5 gm of the deactivated catalyst powder was placed in a small crucible and the crucible, in turn, was placed within a 1 pint (500 ml) wide-mouth jar. Into the bottom of the jar was placed the same stoichiometric amount of ammonium hydroxide that had been used in Example No. 1. The jar was closed and was placed in an oven at 90° C. for 30 minutes. The lid was then removed from the jar and heating was continued for an additional 15 minutes to expel any unadsorbed ammonia or water vapor. Finally, the same amount of concentrated HCl as used in Experiment No. 1 was placed in the bottom of the jar, the lid was replaced and heating for 30 minutes at 90° C. was performed. The lid was removed and the open jar was heated for an additional 15 minutes to expel any unadsorbed vapor. It was noted that, after the NH4OH vapor treatment, the powder assumed a robin's egg blue color and, similarly, after the HCl treatment, the color changed to a yellow with a green tint. The regenerated powder was then coated on Alundum using substantially anhydrous ethanol and was calcined at 320° C. In the activity test of this catalyst utilizing the isobutylene reactant feed and a first stage catalyst, a yield of methacrylic acid of 41.8% was obtained. This result indicated nearly complete activity recovery.

Example No. 3

0.5 gm of the deactivated catalyst which had already been coated on Alundum particles was given the same alternate vapor phase treatments with NH4OH and HCl that was described in Example No. 2. In the activity test utilizing the isobutylene reactant feed and a first stage catalyst, a yield of 46.9% was reached. Again, essentially complete recovery of activity was indicated and the possibility that the recoating procedure made any contribution to recovery was eliminated. This work was repeated and in both instances it was observed that some on-stream time was required for the regenerated catalyst to regain its full activity (29.0% Yield of methacrylic acid after 1 hour and 46.9% after 2.5 hours).

The foregoing method of regeneration is applicable to restoring the activity of catalysts which have suffered extensive crosslinking of acid sites as well as those which have undergone thermal excursion resulting in actual loss of the PMA structure.

As an illustration of the practice of the subject method, a typical case would be where the PMA based catalyst, in a fluid-bed reactor, undergoes deactivation at a rate requiring removal and replacement with fresh catalyst after three months of operation. A slip stream of this catalyst would continuously be removed from the operating reactor, passed through a first fluidizing regenerator vessel, to a second fluidizing regenerator vessel and then to a third fluidizing vessel wherein a finishing calcination is conducted. Following calcining, the regenerated catalyst would be returned to the reactor. Size of each of the separate regenerator vessels would be such that their volume would comprise from 0.01 to 0.001 the volume of the reactor, thereby permitting 2-10 catalyst turn-overs per three month period with a residence time in each regenerator vessel of about one hour.

More specifically, the first regenerator would be fluidized with air at 90° C. while an amount of aqueous ammonia vapor is fed to the reactor at a relative pressure of 0.9 to cause the conversion of the contained molybdenum to ammonium molybdate. The second regenerator would be fluidized with air at 90° C. while an amount of aqueous HCl vapor is fed to the reactor at a relative pressure of 0.9 to cause the effective pH of the fluid phase within the catalyst particles to assume a value of 3–5. Lastly, in the calcination vessel, the temperature of the catalyst would be raised from 90° C. to about 350° C. This treatment will cause the volatilization of all or most of the ammonium chloride associated with the regenerated catalyst to be volatilized prior to reintroducing it to the reactor.

Alternatively, a single regeneration vessel may be used, however, in this instance, the regeneration would be performed in a series of batch operations each separately conducted in the same regenerator. Once the regeneration sequence had been completed, the regenerated catalyst would be returned to the reactor and then another charge of catalyst from the reactor would be transferred for regeneration.

As a second method for regeneration, for instances where the catalyst has been deactivated only by crosslinking, it is possible to hydrolyze the crosslinks and then reprecipitate as the ammonium salt thereby restoring full activity. To demonstrate the efficacy of this method, an experiment was conducted with a deactivated catalyst that had been crosslinked. Activity of the catalyst prior to regeneration was determined to be only 11% Yield of methacrylic acid.

Example No. 4

0.78 gm of the deactivated catalyst powder was dispersed in 10 cc of substantially anhydrous ethanol, heated to boiling (78° C.) and treated with 0.28 cc of 37% HCl solution. After 15 minutes of heating, the pH of the mixture was adjusted to about 5.5 by addition of a 30% NH4OH solution. The resulting slurry was evaporated to near dryness after which drying was continued in an oven at 150° C. The resultant solid was crushed, coated on 2 gms of 10–20 mesh Alundum with the aid of ethanol as a wetting fluid, dried 30 minutes at 150° C. and calcined for 2 hours at 360° C.

In the activity test, utilizing the stacked first and second stage catalyst system presented hereinabove, the regenerated catalyst was employed in a microreactor operating at 375° C. to which was fed 1 part isobutylene, 12 parts air and 3 parts water. The yield of methacrylic acid from isobutylene was 56.36%; a result as good as achieved when fresh catalyst had been employed in similar tests.

While the foregoing methods have been described in conjunction with fluid-bed reactors, either could have further utility if it were applicable for fixed-bed reactor systems. The problem to be overcome first, in the latter system, is that contact of the fixed-bed charge with a specific concentration of base or acid would be difficult due to the fact that the catalyst tends to extract all of the reagent it can accommodate at the point the reagent is introduced, which may be too much, while the catalyst proximal the outlet end may not receive any.

Therefore, treatment of the catalyst with a reagent which does not commence regeneration until having thoroughly contacted the catalyst may be advantageous in such a case. Considering the first method for example, which is dependent upon a certain concentration of ammonia equivalent treating all of the deactivated PMA based catalyst, the required amount may be provided by using a reagent which is only slightly acidic, basic or neutral such as hydrogen cyanide or formamide. Either of these can pass through the fixed-bed catalyst with uniform adsorption. Subsequent hydrolysis under the influence of the strong acid conditions of the acidic catalyst would provide ammonia throughout the catalyst to hydrolyze the cross-links, after which regeneration can proceed.

Based upon the dramatic increases in percent yield of methacrylic acid from methacrolein that have been obtained when a deactivated catalyst has been regenerated by one of the methods set forth herein it should be apparent that the objects of the invention have been met. It is to be understood that the regenerations disclosed herein are applicable in general to PMA based catalysts which, as stated hereinabove, can include one or more promoters. Presence or absence of these additional elements or compounds will not appreciably effect the methods of regeneration set forth herein.

Thus, it should also be apparent to those skilled in the art that the subject invention is operable on PMA based catalysts having various ratios of molybdenum to phosphorous and it is operable when various acids, bases, temperatures and relative pressures are employed. It is to be understood that while these variables fall within the scope of the claimed invention, the subject invention is not to be limited by the examples set forth herein. These have been provided merely to provide a demonstration of operability and it is believed that the selection of specific acids and bases and reaction conditions can be determined without departing from the spirit of the invention herein disclosed and described, and that the scope of the invention shall include all modifications and variations that fall within the scope of the attached claims.

We claim:

1. A method for the regeneration of deactivated phosphomolybdic acid based catalysts comprising the steps of:
   imbibing an aqueous volatile base within the pore structure of said deactivated catalyst so as to form a fluid phase within the pore structure;
   adding hydrochloric acid to said fluid phase so as to form a precipitate; and
   drying and calcining said precipitate to yield a regenerated catalyst.

2. A method for the regeneration of deactivated phosphomolybdic acid based catalysts comprising the steps of:
   imbibing a volatile solvent within the pore structure of said deactivated catalyst so as to form a fluid phase within the pore structure;
   adding hydrochloric acid to said fluid phase;
   adding a volatile base to said fluid phase to form a precipitate; and
   drying and calcining said precipitate to yield a regenerated catalyst.

3. A method for the regeneration of deactivated phosphomolybdic acid based catalysts, as set forth in claims 1 or 2, wherein said volatile base is selected from the group consisting of ammonia, amines and tetraalkyl ammonium hydroxides having from four to about 16 carbon atoms.

4. A method for the regeneration of deactivated phosphomolybdic acid based catalysts, as set forth in claim 3, wherein said volatile base is ammonia.

5. A method for the regeneration of deactivated phosphomolybdic acid based catalysts, as set forth in claims 1 or 2, wherein said deactivated catalyst is supported on a material selected from the group consisting of alumina, Alundum, boron-phosphate, silica, titania and zirconia.

6. A method for the regeneration of deactivated phosphomolybdic acid based catalysts, as set forth in claims 1 or 2, wherein the step of calcining is conducted at a temperature of at least 300° C. for at least one hour.

7. A method for the regeneration of deactivated phosphomolybdic acid based catalysts, as set forth in claim 1, wherein the step of imbibing is conducted at a relative pressure of at least 0.2 up to 0.95.

8. A method for the regeneration of deactivated phosphomolybdic acid based catalysts, as set forth in claims 1 or 2, wherein said phosphomolybdic acid based catalyst has the formula $Mo_xP_yA_aB_bC_cD_dE_eO_z$ wherein A is selected from the group consisting of ammonium, cesium, potassium, rubidium and thallium; B is selected from the group consisting of copper and vanadium; C is selected from the group consisting of antimony, arsenic, bismuth and tellurium; D is palladium; E is aluminum, barium, calcium, cerium, chromium, cobalt, iron, magnesium, manganese, nickel, tantalum, titanium, tungsten, zinc, zirconium, chlorine and/or bromine; x can be 6 to 14; y can be 0.1 to 15; a can be 0.1 to 3; b can be 0.1 to 3; c can be 0 to 2; d can be 0 to 2; e can be 0 to 4 and z is a number necessary to satisfy the valence of all the other elements.

9. A method for the regeneration of deactivated phosphomolybdic acid based catalysts, as set forth in claim 8, wherein x is 12; y is 1 to 1.5; a is 1 to 2; b is 0.1 to 1; c is 0 to 0.7; d is 0 to 1 and e is 0 to 1.

10. A method for the regeneration of deactivated phosphomolybdic acid based catalysts, as set forth in claim 9, wherein the composition of said phosphomolybdic acid based catalyst is $Mo_{12}PAs_{0.5}Cu_{0.25}O_z$.

11. A method for the regeneration of deactivated phosphomolybdic acid based catalysts, as set forth in claims 1 or 2, wherein said regeneration is conducted at a temperature of from about 50° C. to about 200° C.

12. A method for the regeneration of deactivated phosphomolybdic acid based catalysts comprising the steps of:
   imbibing a substantially anhydrous alkyl alcohol having from one to about five carbon atoms within the pore structure of said deactivated catalyst so as to form a fluid phase within the pore structure;
   adding a volatile acid to said fluid phase;
   adding a volatile base to said fluid phase to form a precipitate; and
   drying and calcining said precipitate to yield a regenerated catalyst.

13. A method for the regeneration of phosphomolybdic acid based catalysts comprising the steps of:
   imbibing an aqueous volatile base within the pore structure of said deactivated catalyst so as to form a fluid phase within the pore structure;
   adding a volatile acid, selected from the group consisting of hydrochloric, hydrobromic, hydroiodic, organic carboxylic acids and halogenated carboxylic acids having from 1 to about 4 carbon atoms, to said fluid phase so as to form a precipitate; and
   drying and calcining said precipitate to yield a regenerated catalyst.

14. A method for the regeneration of deactivated phosphomolybdic acid based catalysts comprising the steps of:
   imbibing a volatile solvent within the pore structure of said deactivated catalyst so as to form a fluid phase within the pore structure;

adding a volatile acid, selected from the group consisting of hydrochloric, hydrobromic, hydroiodic, organic carboxylic acids and halogenated carboxylic acids having from 1 to about 4 carbon atoms, to said fluid phase adding a volatile base to said fluid phase to form a precipitate; and drying and calcining said precipitate to yield a regenerated catalyst.

15. A method for the regeneration of deactivated phosphomolybdic acid based catalysts, as set forth in claims 13 or 14, wherein said volatile acid is hydrochloric acid.

16. A method for the regeneration of deactivated phosphomolybdic acid based catalysts as set forth in claims 13 or 14, wherein said volatile base is selected from the group consisting of ammonia, amines and tetraalkyl ammonium hydroxides having from four to about 16 carbon atoms.

17. A method for the regeneration of deactivated phosphomolybdic acid based catalysts, as set forth in claim 16, wherein said volatile base is ammonia.

18. A method for the regeneration of deactivated phosphomolybdic acid based catalysts, as set forth in claims 13 or 14, wherein said deactivated catalyst is supported on a material selected from the group consisting of alumina, Alundum, boron-phosphate, silica, titania and zirconia.

19. A method for the regeneration of deactivated phosphomolybdic acid based catalysts, as set forth in claims 13 or 14, wherein the steps of calcining is conducted at a temperature of at least 300° C. for at least one hour.

20. A method for the regeneration of deactivated phosphomolybdic acid based catalysts, as set forth in claim 13, wherein the step of imbibing is conducted at a relative pressure of at least 0.2 up to 0.95.

21. A method for the regeneration of deactivated phosphomolybdic acid based catalysts, as set forth in claims 13 or 14, wherein said phosphomolybdic acid based catalyst has the formula $Mo_xP_yA_aB_bC_cD_dE_eO_z$ wherein A is selected from the group consisting of ammonium, cesium, potassium, rubidium and thallium; B is selected from the group consisting of copper and vanadium; C is selected from the group consisting of antimony, arsenic, bismuth and tellurium; D is palladium; E is aluminum, barium, calcium, cerium, chromium, cobalt, iron, magnesium, manganese, nickel, tantalum, titanium, tungsten, zinc, zirconium, chlorine and/or bromine; x can be 6 to 14; y can be 0.1 to 15; a can be 0.1 to 3; b can be 0.1 to 3; c can be 0 to 2; d can be 0 to 2; e can be 0 to 4 and z is a number necessary to satisfy the valence of all the other elements.

22. A method for the regeneration of deactivated phosphomolybdic acid based catalysts, as set forth in claim 21, wherein x is 12; y is 1 to 1.5; a is 1 to 2; b is 0.1 to 1; c is 0 to 0.7; d is 0 to 1 and e is 0 to 1.

23. A method for the regeneration of deactivated phosphomolybdic acid based catalysts, as set forth in claim 22, wherein the composition of said phosphomolybdic acid based catalyst is $Mo_{12}PAs_{0.5}Cu_{0.25}O_z$.

24. A method for the regeneration of deactivated phosphomolybdic acid based catalysts, as set forth in claims 13 or 14, wherein said regeneration is conducted at a temperature of from about 50° C. to about 200° C.

25. A method for the regeneration of deactivated phosphomolybdic acid based catalysts, as set forth in claim 14, wherein said volatile solvent is a substantially anhydrous alkyl alcohol having from one to about five carbon atoms.

* * * * *